United States Patent [19]

Suga

[11] Patent Number: 5,530,030
[45] Date of Patent: Jun. 25, 1996

[54] NEMATICIDES AGAINST PINE WOOD NEMATODES

[75] Inventor: Takayuki Suga, Hiroshima, Japan

[73] Assignee: Kioritz Corporatin, Tokyo, Japan

[21] Appl. No.: 327,277

[22] Filed: Oct. 21, 1994

[30] Foreign Application Priority Data

Oct. 25, 1993 [JP] Japan ................. 5-266444

[51] Int. Cl.⁶ .......................... A61K 31/055; A01N 31/08
[52] U.S. Cl. ......................... 514/731; 424/196.1
[58] Field of Search ................... 514/724, 730, 514/731, 456; 424/196.1

[56] References Cited

U.S. PATENT DOCUMENTS

| | | | |
|---|---|---|---|
| 2,854,375 | 9/1958 | Shackell | 514/731 |
| 3,692,916 | 9/1972 | La Barbera | 514/731 |
| 3,833,736 | 9/1974 | Frick | 514/724 |
| 3,930,025 | 12/1975 | Albright et al. | 514/731 |
| 5,314,693 | 5/1994 | Suga | 424/196 |

FOREIGN PATENT DOCUMENTS 63-104905  5/1988  Japan.
63-159302  7/1988  Japan.
63-264510  11/1988  Japan.
3-52805  3/1991  Japan.

OTHER PUBLICATIONS

Chem. Pharm. Bull. 40(5) 1130 (1992), Mohammad Ahad Ali et al. "Synthesis and Nematocidal Activity of Hydroxystilbenes".
Chemical Abstracts 78, 48(1973) 155087t; Gibbs, J. N.
Chemical Abstracts 88, 134(1978)116230w; Gorham, John.
Chemical Abstracts 111, 434(1989) 171162u, Koichiro et al.

Primary Examiner—Werren B. Lone
Attorney, Agent, or Firm—David G. Conlin; George W. Neuner

[57] ABSTRACT

Highly effective nematicides against pine wood nematodes containing chlorinated hydroxystilbene or salts thereof (preferably, 3',4'-Dichloro-3-hydroxystilbene and 3',5'-dichloro-3-hydroxystilbene) which are prepared by synthesizing chlorinated methoxystilbenes from chlorinated benzyl chloride compounds and methoxybenzaldehydes by the Wittig-Horner reaction, performing demethylation to obtain the chlorinated hydroxystilbenes, and preparing the salts thereof by conventional methods, if necessary.

3 Claims, 15 Drawing Sheets

NEMATICIDES AGAINST PINE WOOD NEMATODES

BACKGROUND OF THE INVENTION

The present invention relates to a nematicide against pine wood nematodes (*Bursaphelenchus xylophilus* Mamiya and Kiyohara, etc.), and more particularly to an nematicide against pine wood nematodes containing a chlorinated hydroxystilbene. Further, the present invention relates to a method for synthesizing chlorinated hydroxystilbenes. Furthermore, the present invention relates to novel chlorinated hydroxystilbenes.

Pine wood nematodes have caused heavy damage, the dying of pine trees, in various places in Japan, which has posed a serious social problem. It has been well known that pine wood nematodes, fungivorous nematodes, enter pine wood tissues and propagate to cause pine trees to die.

The mechanism by which the pine wood nematodes cause the pine trees to die is considered as follows:

a) In the pine trees infected with the pine wood nematodes are produced toxins (phytoalexins) such as benzoic acid (1), catechol (2), dihydroconiferyl alcohol (3), 8-hydroxycarvotanacetone (4) and 10-hydroxyverbenone (5), b) The nematodes secrete cellulase, c) Tracheids of the pine trees are clogged with α-pinene and β-pinene abnormally accumulated after the nematode infection, and d) Toxins are secreted by molds which propagate in the pine trees after the nematode infection.

The pine wood nematodes are transmitted to the pine trees through injurious insects such as a pine sawyer (*Monochamus alternatus* Hope).

Previous methods for preventing the pine trees from dying by the pine wood nematodes mainly include (1) cutting down damaged trees to exterminate ova, pupae and adults present in the damaged trees before the pine sawyers carrying nematodes, which are directly responsible for the death of the pine trees, escape from the damaged trees, and (2) applying insecticides (sprinkling and cropdusting) for preventing maturing feeding after eclosion and escape of the pine sawyers. The insecticides used herein include organic phosphorus pesticides, NAC agents (1-naphthyl-N-methylcarbamate), PAP agents (ethyl dimethyl-dithiophosphorylphenylacetate), EDB agents (1,2-dibromoethyl), MPP agents (O,O-dimethyl-O-[3-methyl-4-(methylthio)phenyl] thiophosphate) and MEP agents (dimethyl(3-methyl-4-nitrophenyl) thiophosphate).

In addition to the above-mentioned insecticides for the pine sawyers, nematicides for directly exterminating the pine wood nematodes in the pine trees include a levamisole hydrochloride agent containing levamisole hydrochloride as a main insecticidal ingredient (trade name: "Century", Mitsubishi Petrochemical Co. Ltd., Japan), a mesulfenfos agent (trade name: "Nemanon", Nihon Bayer Agro Chem. K/K, Japan) and a morantel tartrate agent (trade name: "Greenguard", Fizer Pharmaceutical Inc., Japan).

The previous methods for exterminating the pine sawyers have the following problems:

(1) A great deal of labor is required.

(2) It is difficult to decide the suitable time of insecticide application because the time of emergence and escape of the pine sawyers differs from year to year.

(3) The effectiveness of the insecticides has become lowered.

(4) In order to achieve the exterminating effect in forests and fields, the dosage per unit area is required to be 10 times that generally used in agriculture.

(5) Social problems such as the remaining of the given insecticides in soil, the remaining in water systems and the effect on ecosystems such as surrounding animals and plants are encountered. The sufficient controlling effect can not be attained because of these problems.

(6) The previous insecticides for directly exterminating the pine wood nematodes in wood are effective, but have a problem in safety because of their toxicity.

The present inventor previously discovered that the nematicidal active substances against the pine wood nematodes were present in *Pinus strobus*, *Pinus palustris* and *Pinus massoniana* which were said to have a resistance to the pine wood nematodes, and found pinosylvin monomethyl ether (compound 1, see Table 3) which is a hydroxystilbene, as one of the active substances. The present inventor already filed an application for the nematicide containing this compound (UK Published Application No. GB 2263869 A; German Unexamined Patent Publication No. DE 4303346 A1; U.S. Pat. No. 5,314,693).

SUMMARY OF THE INVENTION

As a result of further studies on hydroxystilbenes occurring in nature, the present inventor discovered that chlorinated hydroxystilbenes having the same carbon skeleton as that of pinosylvin monomethyl ether (compound 1) exhibited an excellent nematicidal activity against the pine wood nematodes, thus completing the present invention.

The present invention provides (1) a nematicide against pine wood nematodes containing a chlorinated hydroxystilbene or a salt thereof; (2) the nematicide described (1), wherein the chlorinated hydroxystilbene is 2'-chloro-3-hydroxystilbene, 3'-chloro-3-hydroxystilbene, 4'-chloro-3-hydroxystilbene, 3',4'-dichloro-3-hydroxystilbene or 3',5'-dichloro-3-hydroxystilbene; (3) a method for preparing a chlorinated hydroxystilbene or a salt thereof comprising synthesizing a chlorinated methoxystilbene from a chlorinated benzyl chloride compound and a methoxybenzaldehyde by the Wittig-Horner reaction, performing demethylation to obtain the chlorinated hydroxystilbene, and preparing the salt thereof by a conventional method, if necessary; and (4) 3',4'-dichloro- 3-hydroxystilbene or 3',5'-dichloro-3-hydroxystilbene.

BRIEF DESCRIPTION OF THE DRAWINGS

FIGS. 3-1 to 3-3 is a $^1$H NMR spectral diagram of 2'-chloro-3-hydroxystilbene (compound 3);

FIGS. 5-1 to 5-3 is a $^1$H NMR spectral diagram of 3'-chloro-3-hydroxystilbene (compound 4);

DESCRIPTION OF THE PREFERRED EMBODIMENTS

Figure 1:
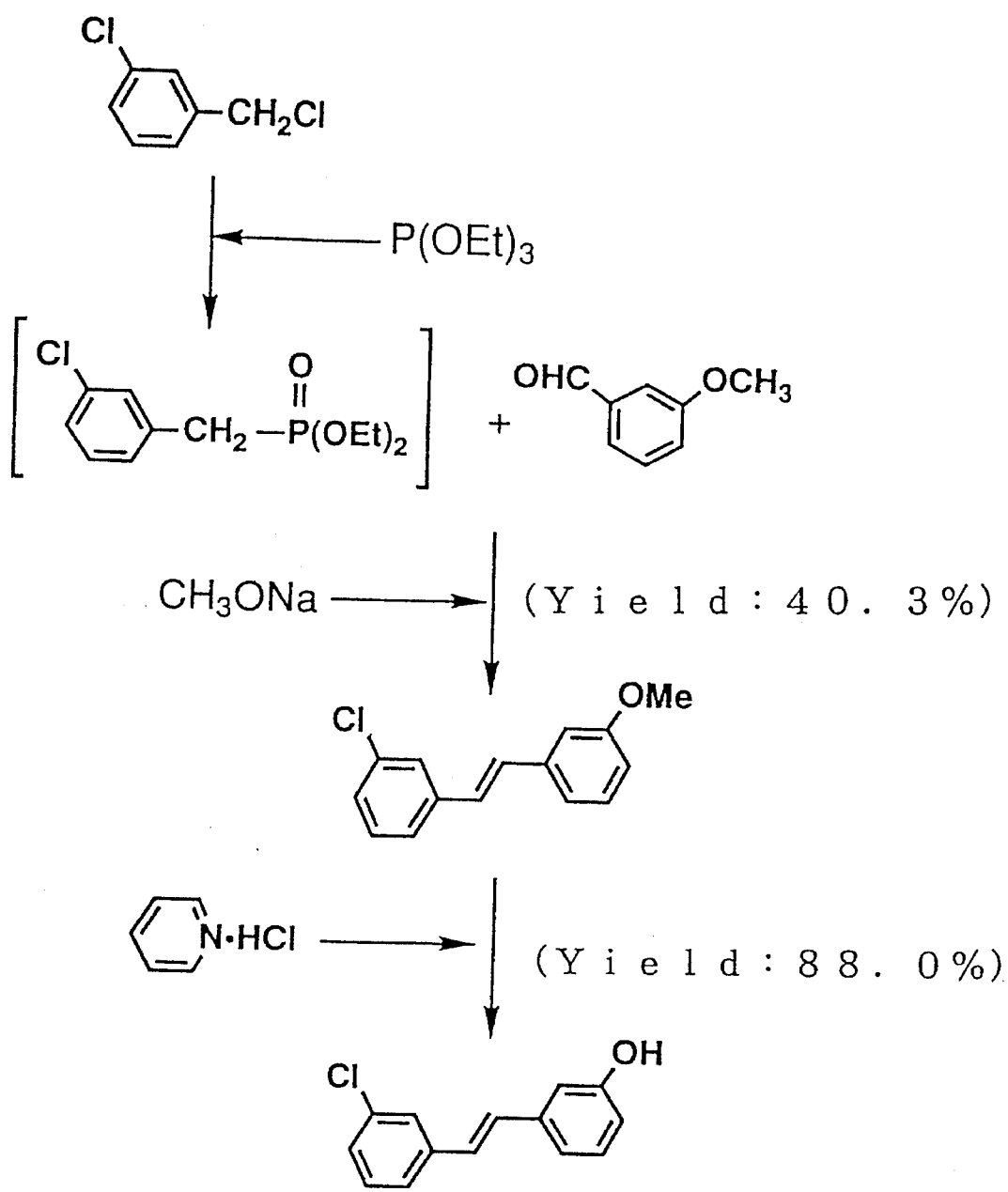
FIG. 1 shows a reaction formula for illustrating a method of synthesizing a chlorinated hydroxystilbene of the present invention.
Figure 2:
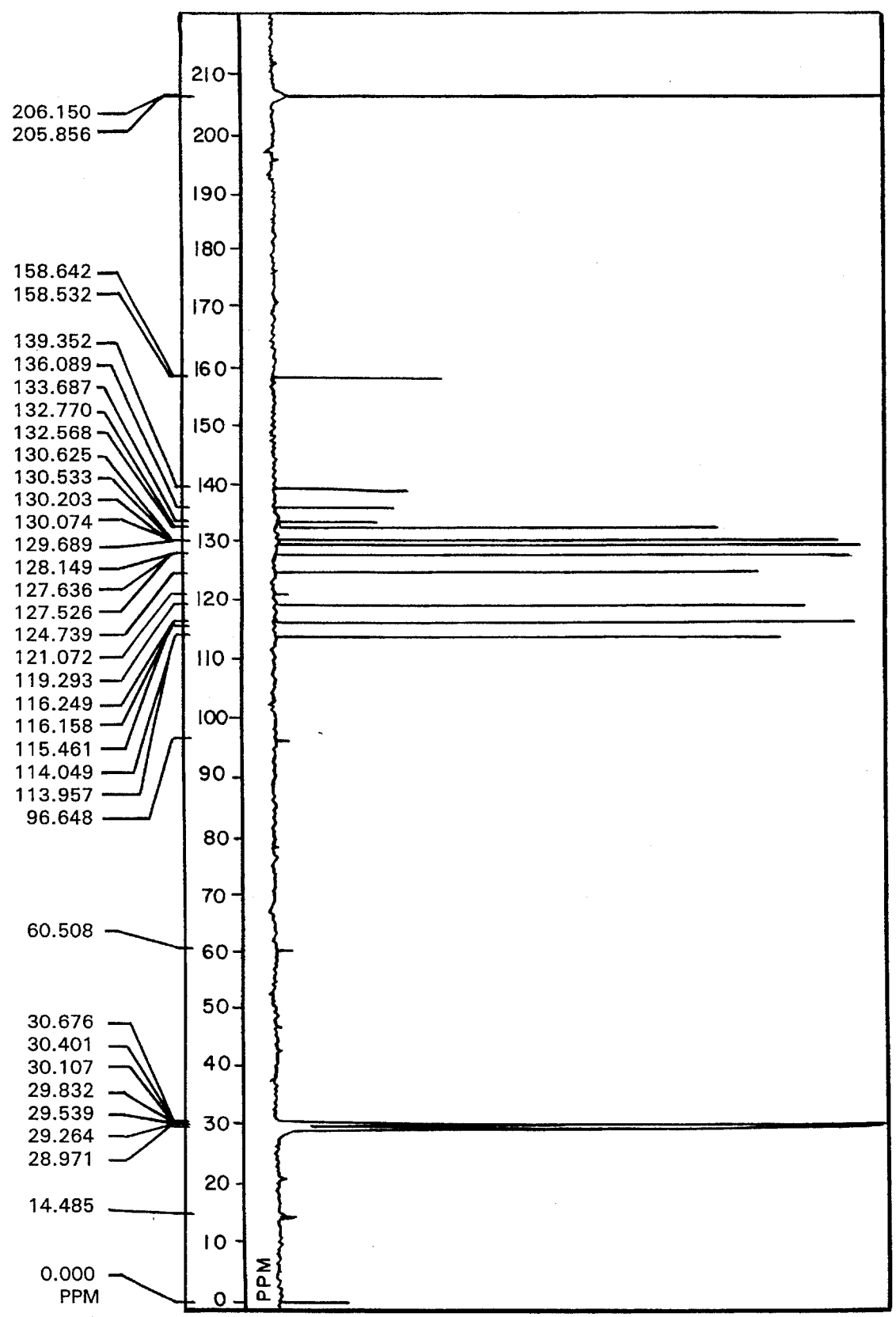
FIG. 2 is a $^{13}$C NMR spectral diagram of 2'-chloro-3-hydroxystilbene (compound 3)
Figures 1, 3:
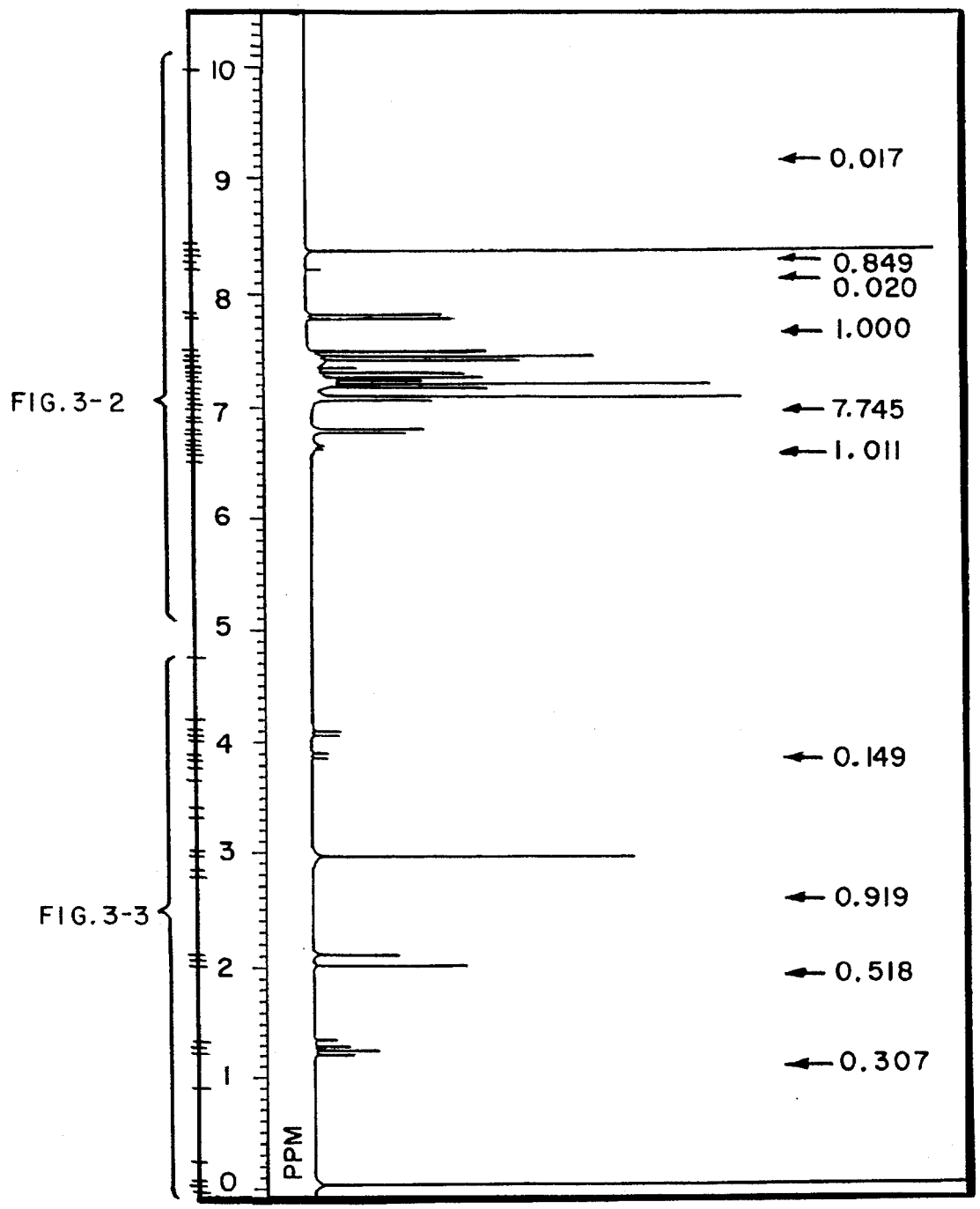
Figures 2, 3:
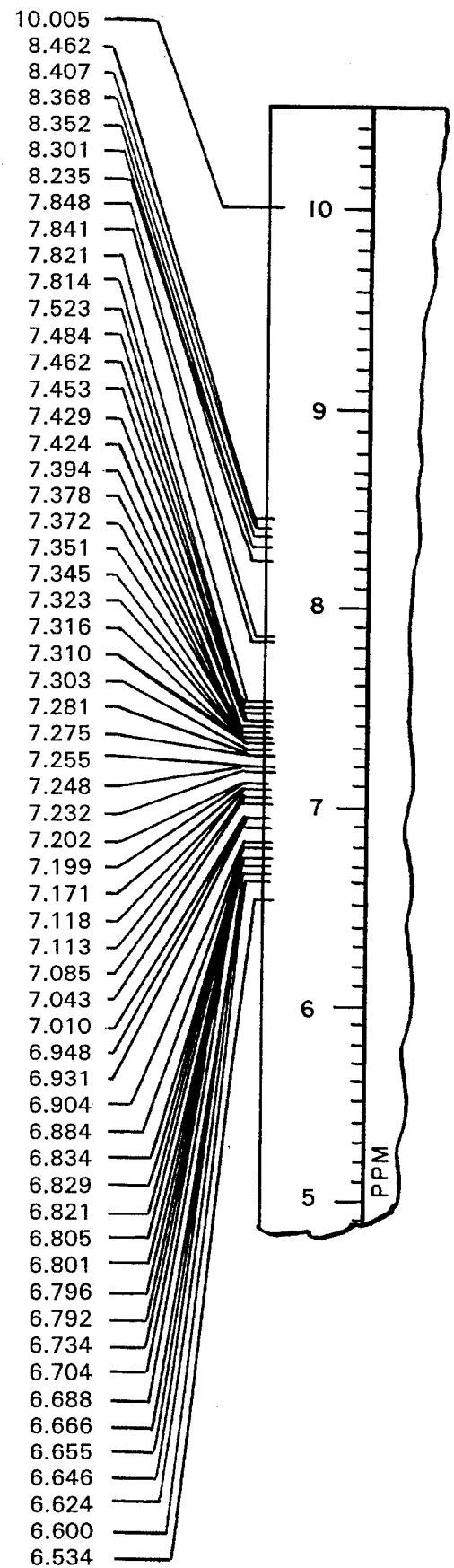
Figure 3:
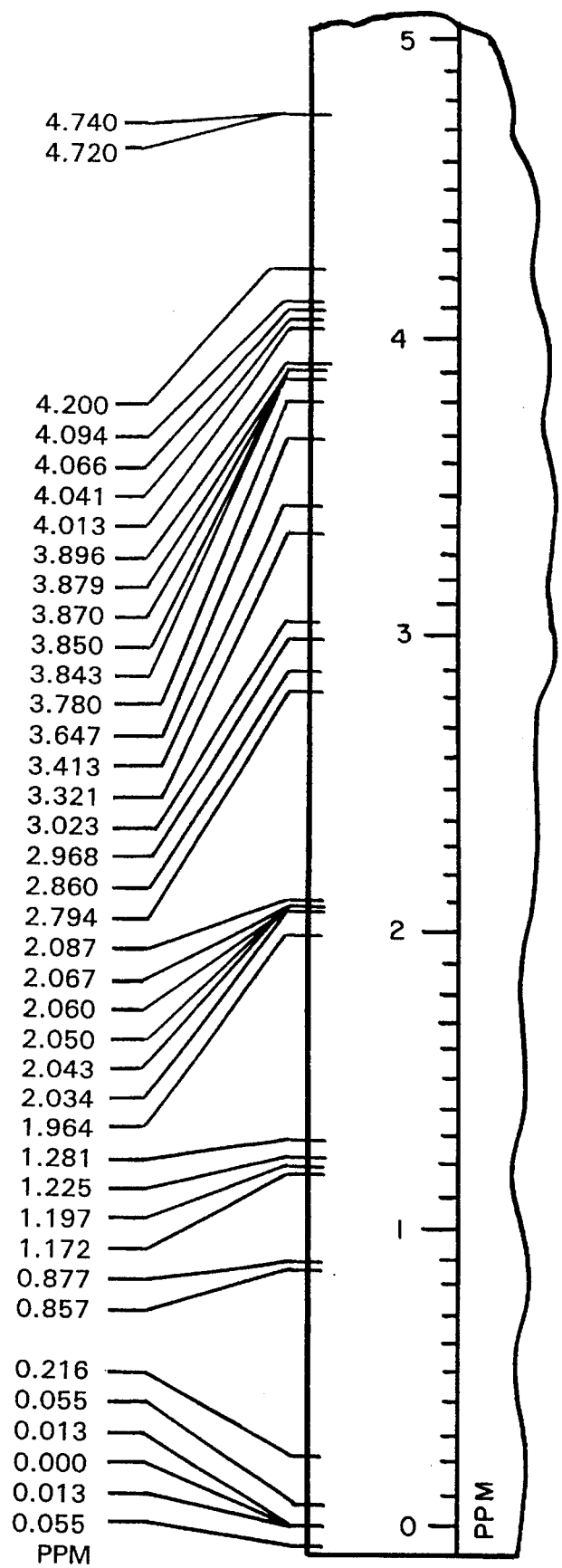
Figure 4:
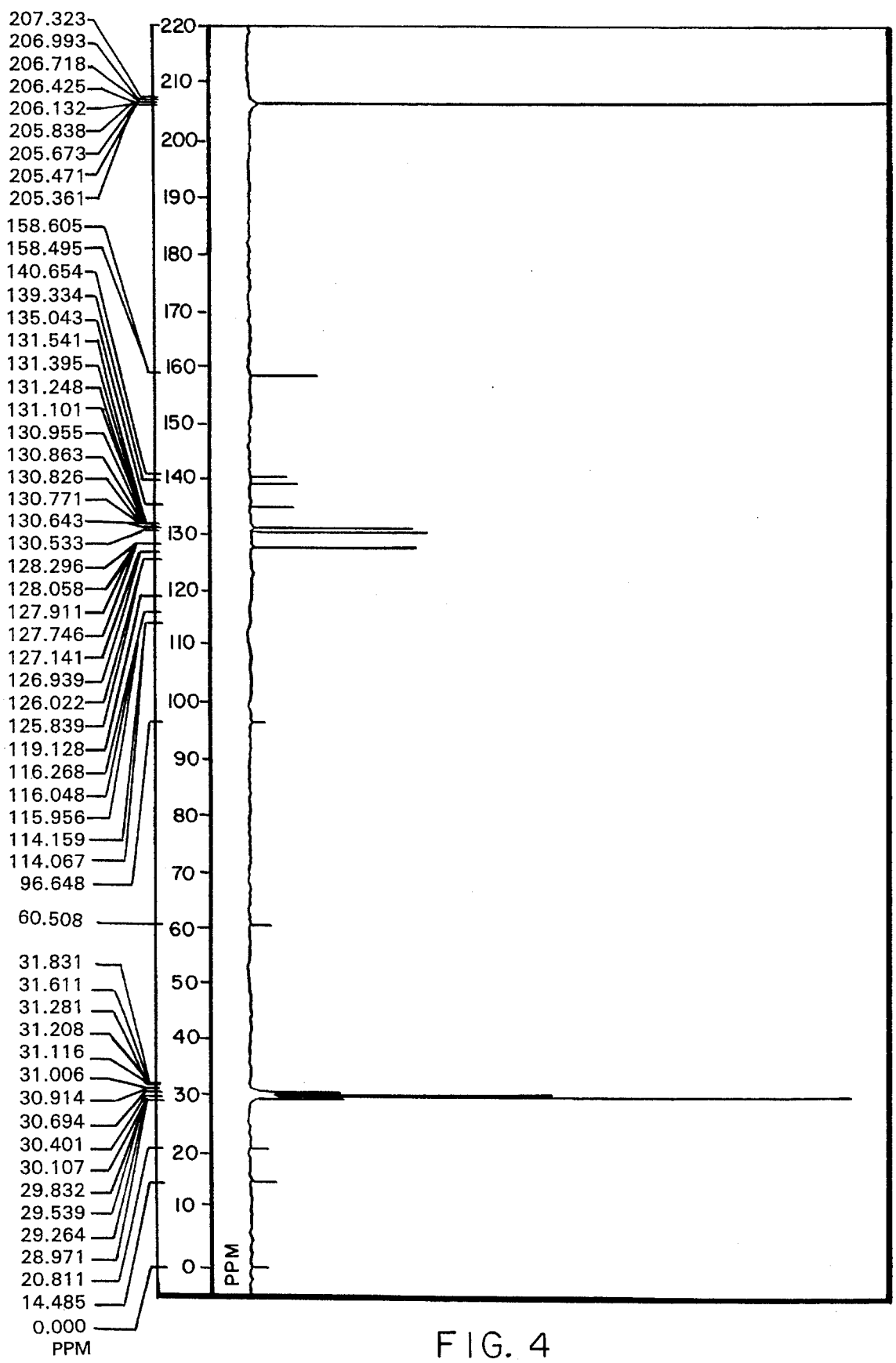
FIG. 4 is a $^{13}$C NMR spectral diagram of 3'-chloro-3-hydroxystilbene (compound 4)
Figures 1, 5:
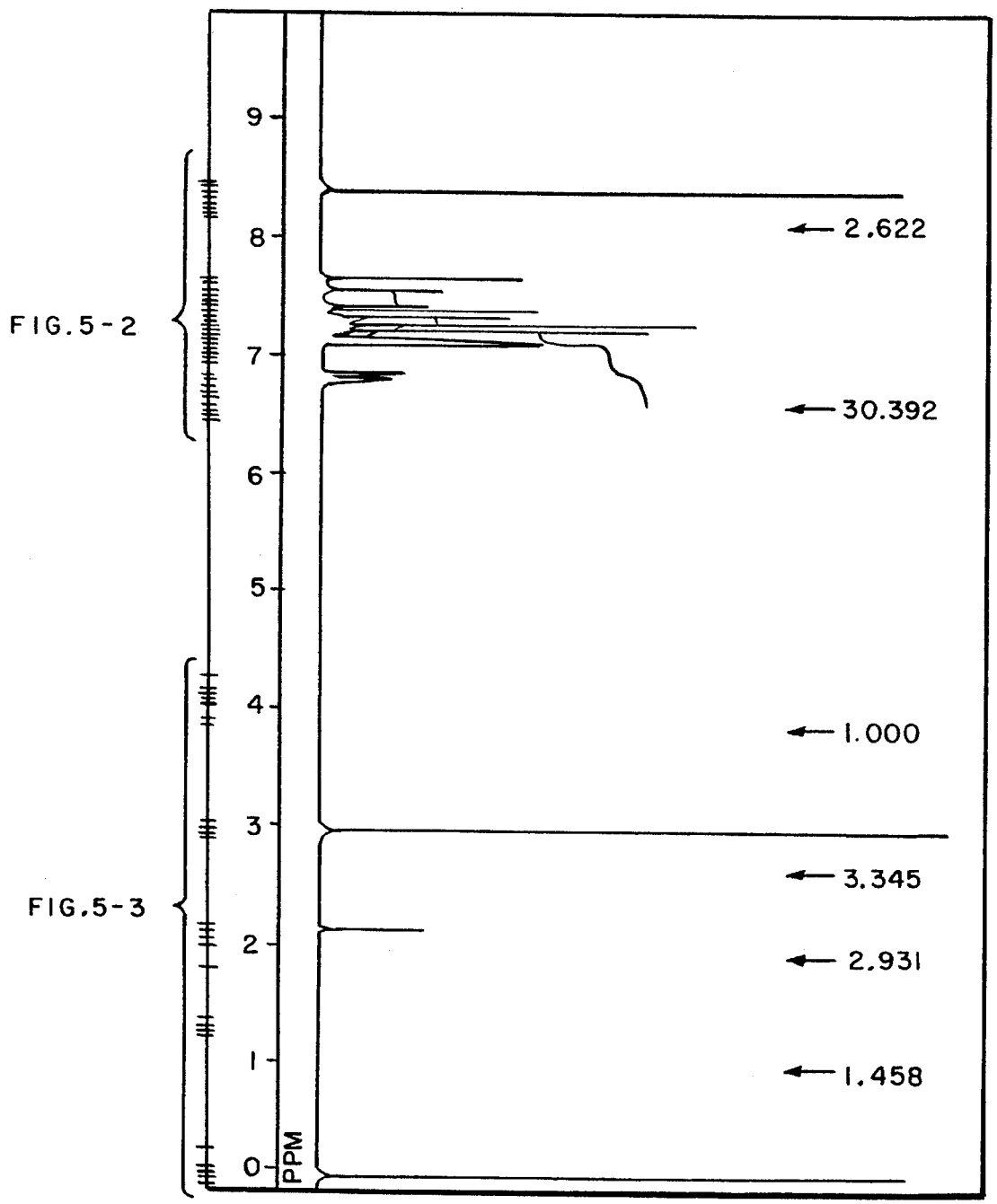
Figures 2, 5:
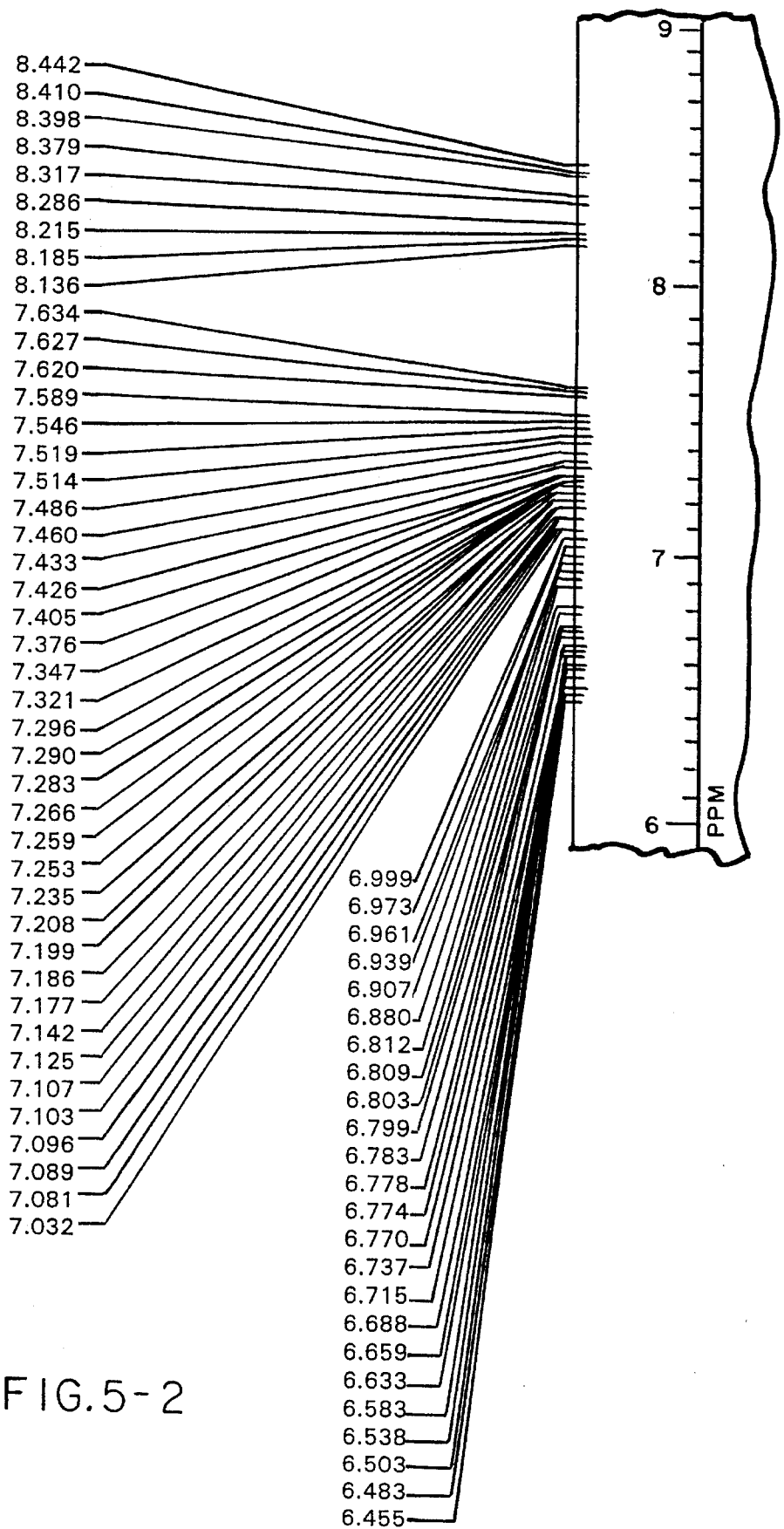
Figures 3, 5:
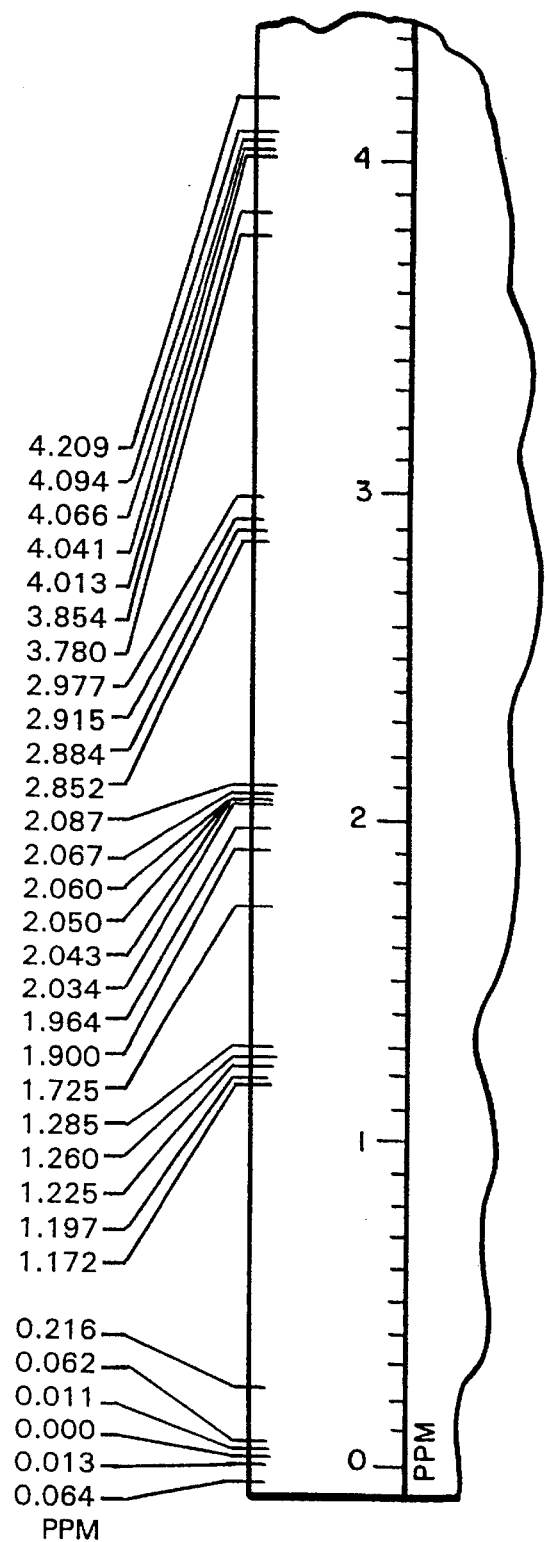
Figure 6:
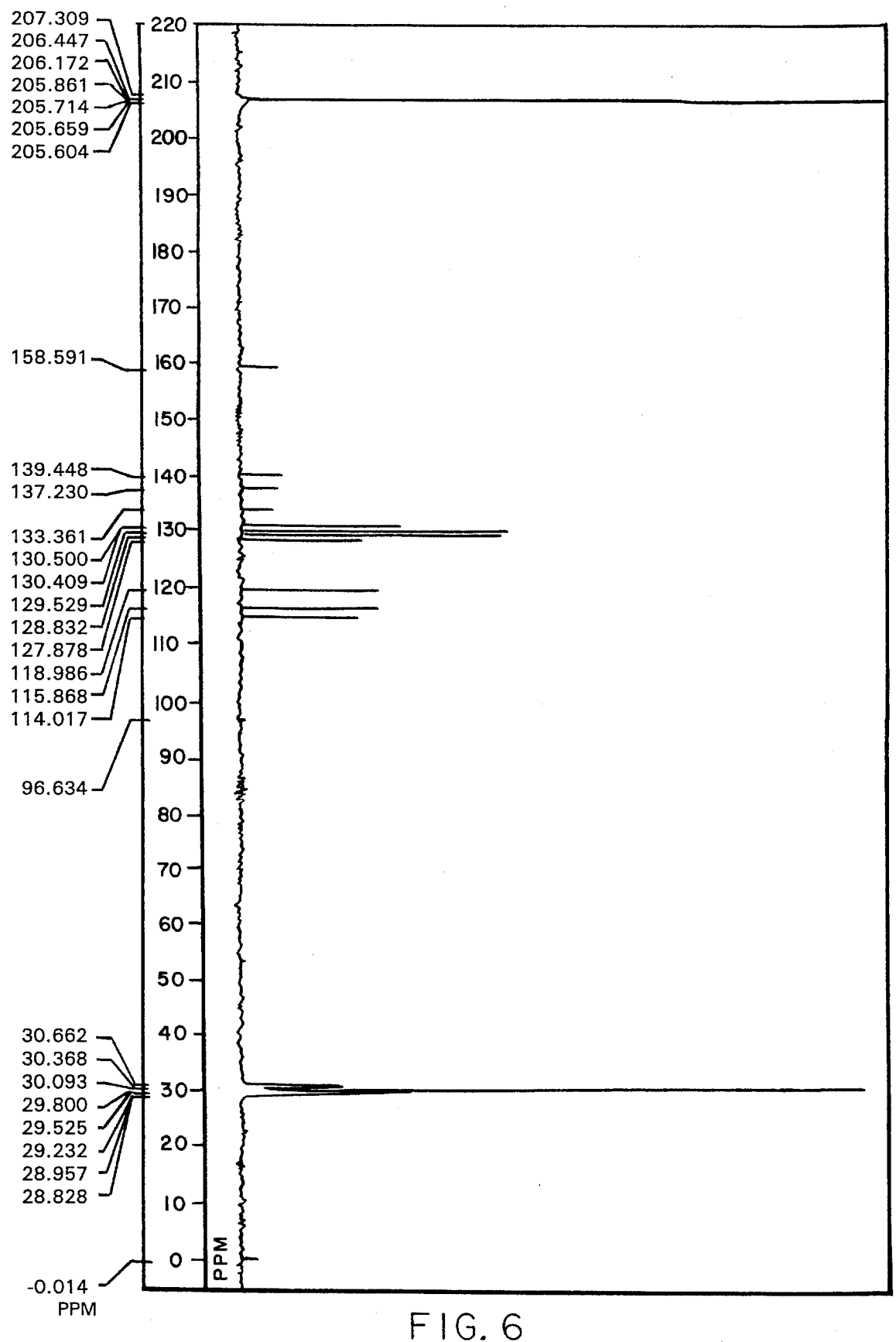
FIG. 6 is a $^{13}$C NMR spectral diagram of 4'-chloro-3-hydroxystilbene (compound 5)
Figure 7:
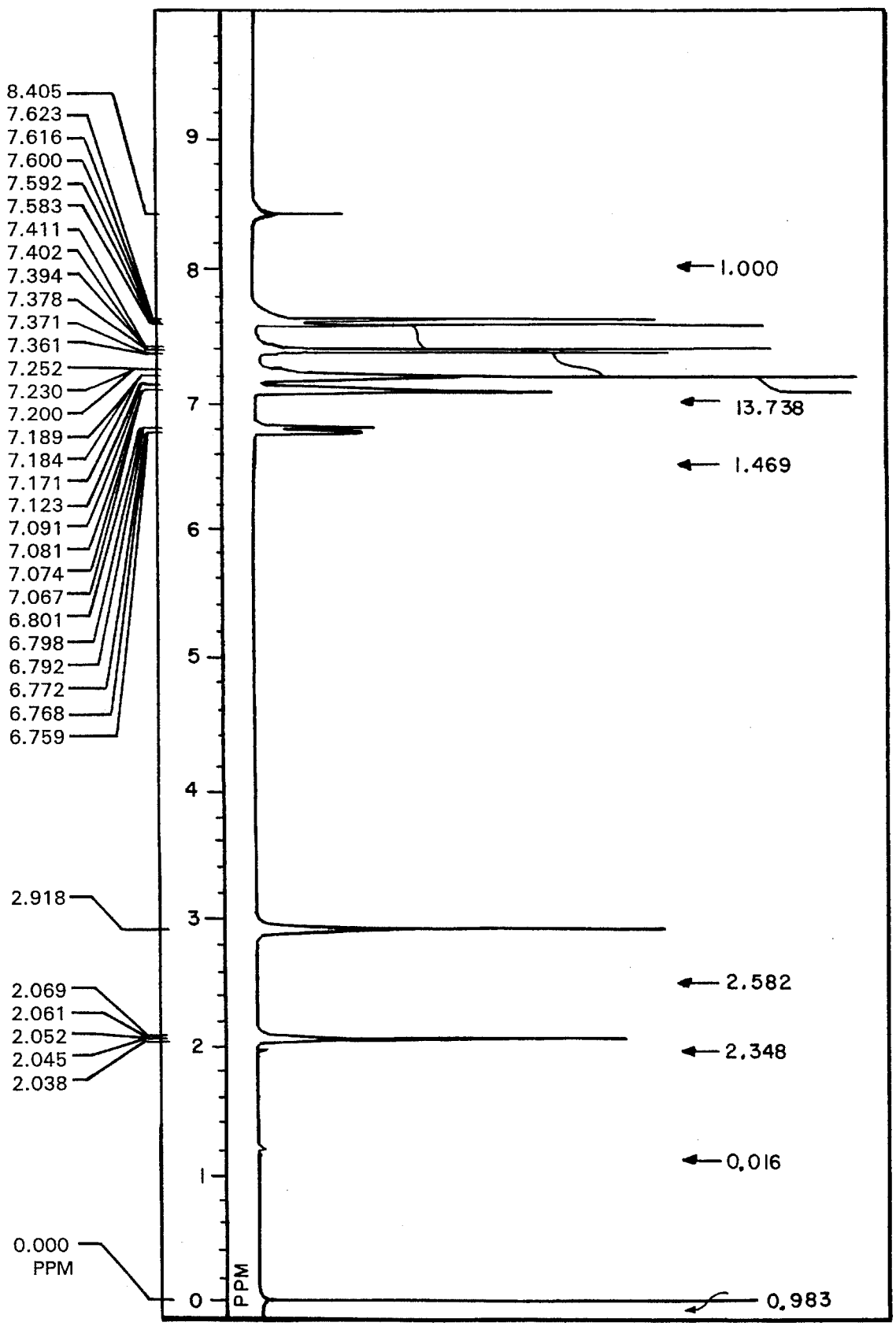
FIG. 7 is a $^1$H NMR spectral diagram of 4'-chloro-3-hydroxystilbene (compound 5)
Figure 8:
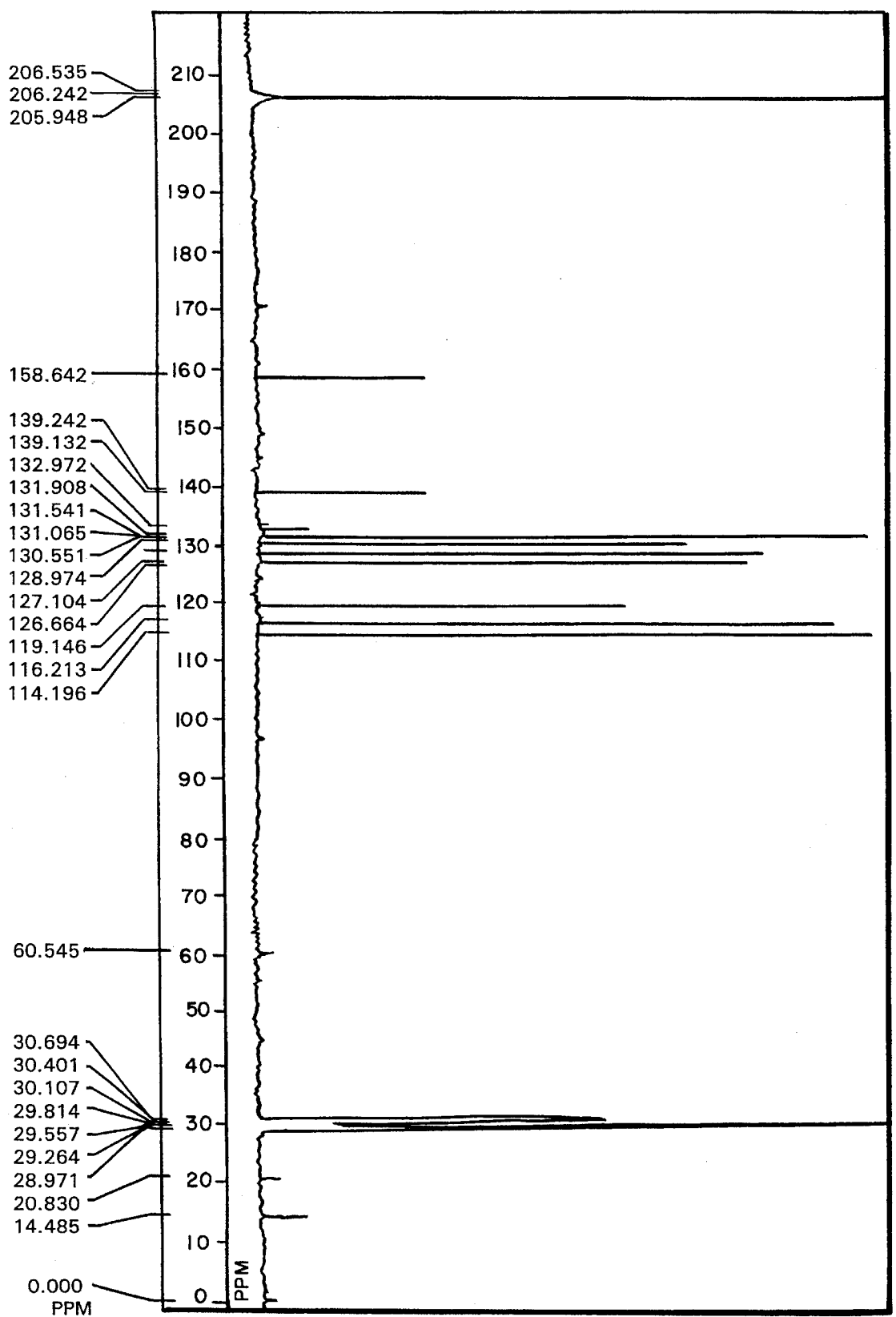
FIG. 8 is a $^{13}$C NMR spectral diagram of 3',4'-dichloro-3-hydroxystilbene (compound 6)
Figure 9:
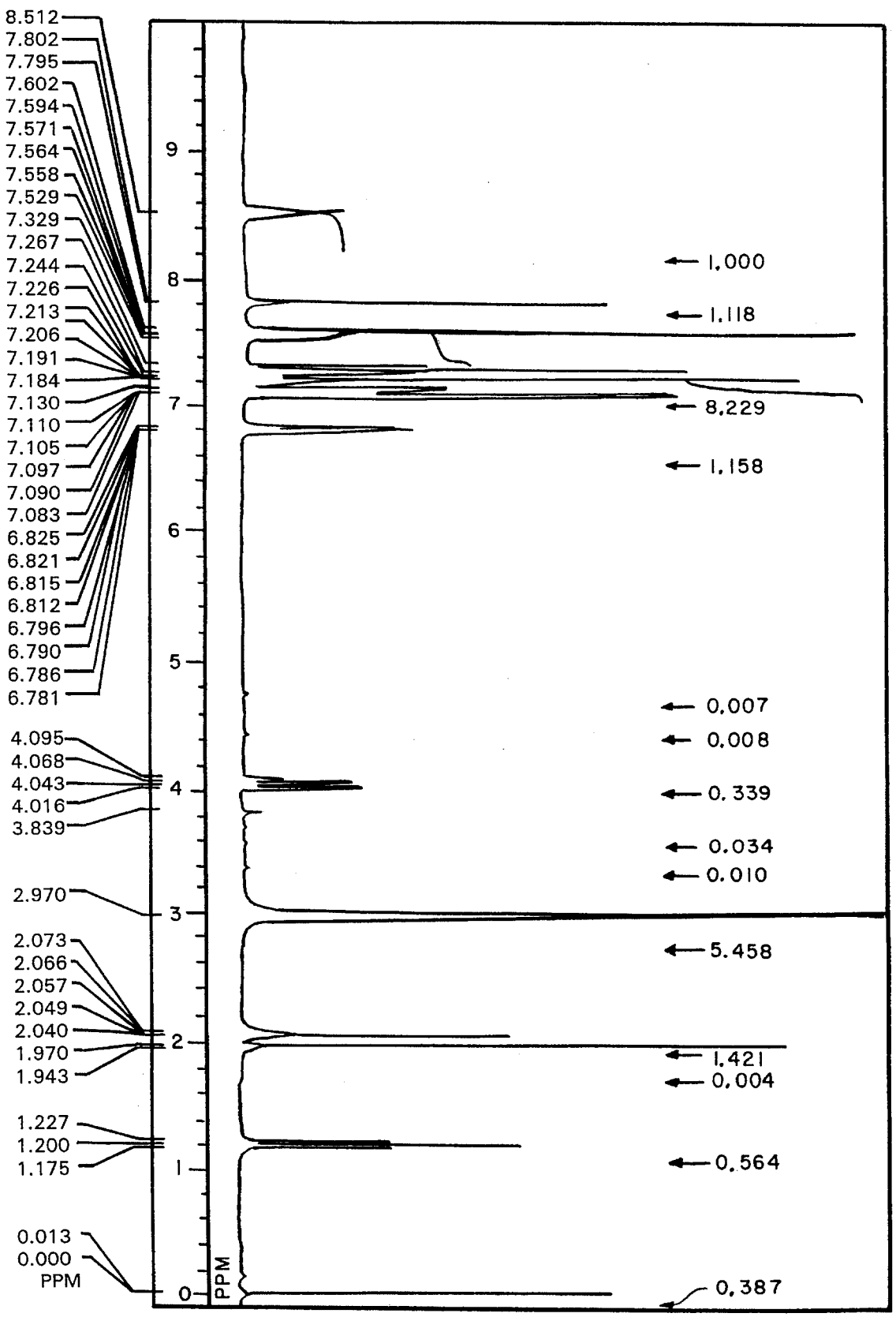
FIG. 9 is a $^1$H NMR spectral diagram of 3',4'-dichloro-3-hydroxystilbene (compound 6)
Figure 10:
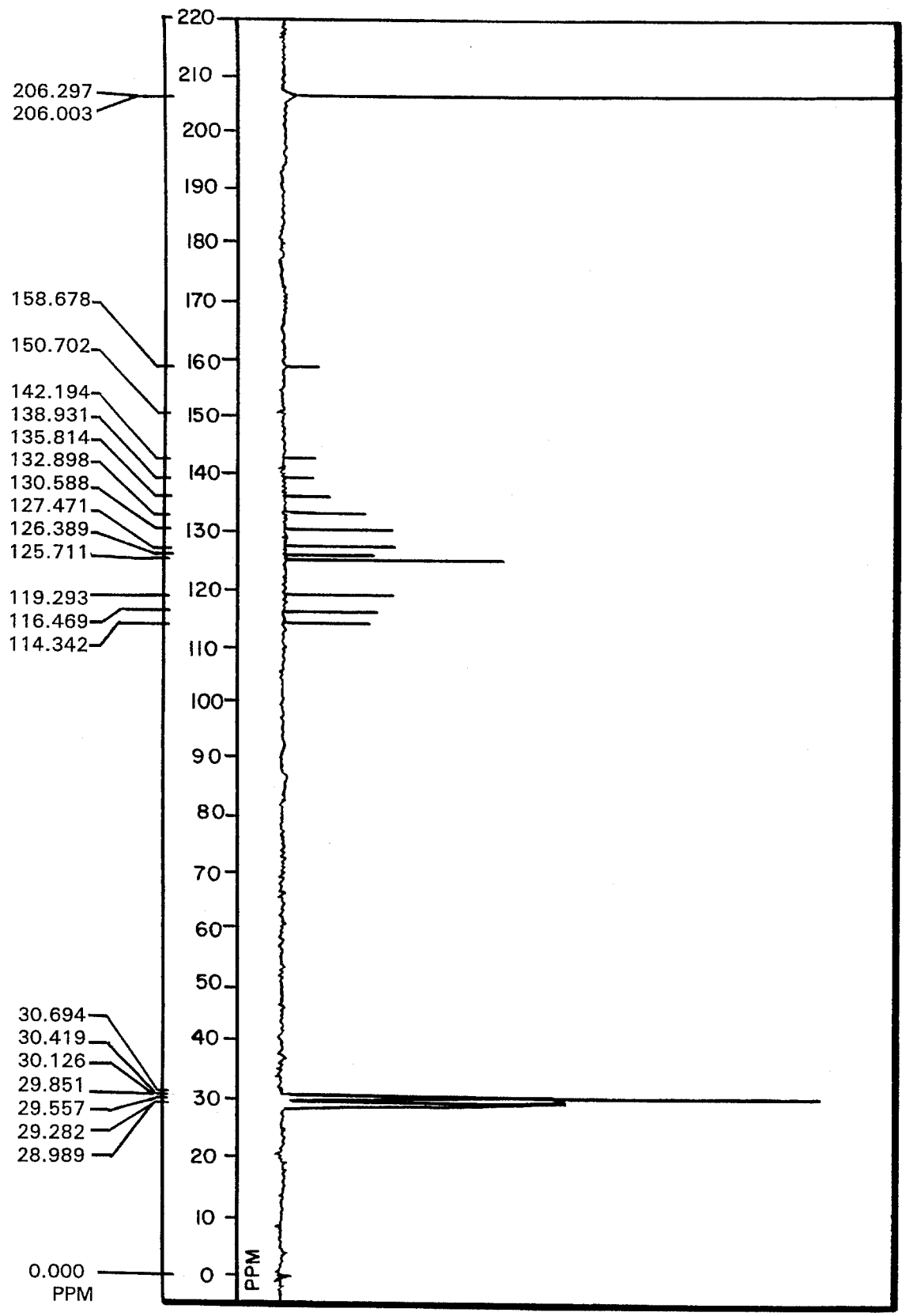
FIG. 10 is a $^{13}$C NMR spectral diagram of 3',5'-dichloro-3-hydroxystilbene (compound 7)
Figure 11:
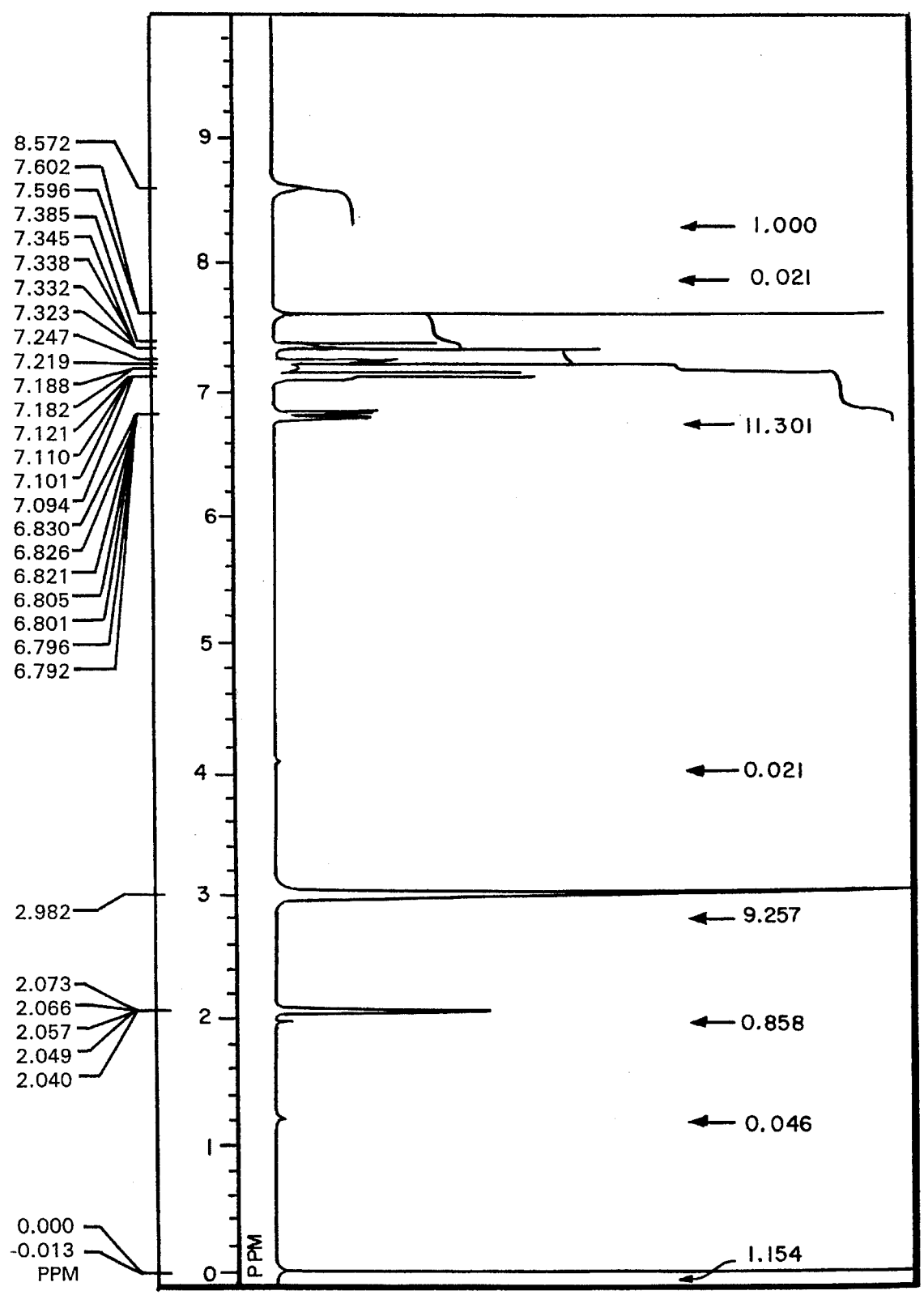
FIG. 11 is a $^1$H NMR spectral diagram of 3',5'-dichloro-3-hydroxystilbene (compound 7).

The chlorinated hydroxystilbenes and the salts thereof used in the present invention include hydroxystilbenes in each of which 1 to 9 chlorine atoms are added to a benzene ring, and sodium salts and potassium salts thereof. Examples thereof include 2'-chloro-3-hydroxystilbene (compound 3, see Tables 2 and 3, hereinafter the same), 3'-chloro- 3-hydroxystilbene (compound 4), 4'-chloro-3-hydroxystilbene (compound 5), 3',4'-dichloro-3-hydroxystilbene (compound 6), 3',5'-dichloro-3-hydroxystilbene (compound 7), and sodium salts and potassium salts thereof.

Of the above-mentioned chlorinated hydroxystilbenes, compounds 6 and 7 are novel compounds and have an excellent nematicidal activity against the pine wood nematodes as described above.

The synthesis of the chlorinated hydroxystilbene of the present invention is conducted by synthesizing a chlorinated methoxystilbene from a chlorinated benzyl chloride compound and a methoxybenzaldehyde corresponding to the desired chlorinated hydroxystilbene by the Wittig-Horner reaction, and performing demethylation with a demethylating agent. In the Wittig-Horner reaction, the chlorinated benzyl chloride, a starting material, is first converted to a phosphonate, which is reacted with the methoxybenzaldehyde in the presence of a base to obtain the chlorinated methoxystilbene. The resulting chlorinated methoxystilbene is demethylated in the presence of a base such as NaOMe, KOMe, NaOEt and KOEt to obtain the desired chlorinated hydroxystilbene. In demethylation reaction Lewis acid such as pyridinium chloride or boron tribromide can be used. Then, the salts thereof can be produced by conventional methods such as reaction with alkali hydroxides, for example, sodium hydroxide and potassium hydroxide, if necessary.

The nematicides containing these compounds having the nematicidal activity as main ingredients can contain these active ingredients in any desired amounts, for example, about 1 to 10%, in combination with other known carriers, additives, etc.

As the carriers of pest control chemicals including the repellents and the nematicides against the pine wood nematodes of the present invention, liquid carriers or solid carriers are used depending on the purpose of their use.

The liquid carriers include water, alcohols, ketones, ethers, aromatic hydrocarbons, acid amides and esters. The solid carriers include known solid carriers such as mineral powders, alumina, sulfur powder and active carbon.

For the formulation, the pest control chemicals can be used as injection and cataplasm. These preparations may contain emulsifiers, suspensions, stabilizers, stickers, penetrants and dispersing agents, if necessary, and can be prepared by methods known in the art.

The following example is given by way of illustration and is not to be construed as a limitation of the invention.

EXAMPLE 1

Syntheses of Chlorinated Hydroxystilbenes

Compounds 3 to 7 can be synthesized by the Wittig-Horner reaction, arbitrarily changing starting materials (a) and (c) shown in Table 1. Here, the synthesis of 3'-chloro-3-hydroxystilbene is described as an example (see FIG. 1).

An excess of triethyl phosphite was added to 3-chlorobenzyl chloride (a), and the mixture was heated with stirring at 130° C. until the generation of ethyl bromide stopped. Diethylchlorobenzyl phosphonate (b) was obtained by the removal of excess triethyl phosphite. Dried dimethylformamide and an excess of sodium methylate were added thereto as a solvent and as a base, respectively, followed by cooling at 0° C. on an ice bath. An equivalent of m-anisaldehyde (c) was added thereto, and the mixture was stirred at room temperature for 1 hour. Then, after stirring at 90° C. for 1 hour, the temperature was lowered to room temperature and stirring was continued overnight. The reaction solution was extracted with ethyl acetate to obtain an ethyl acetate extract. This extract was purified by silica gel chromatography (solvent: hexane/ethyl acetate=9.5/0.5 (V/V)) to obtain 3'-chloro-3-methoxystilbene (d). Subsequently, an excess of pyridinium chloride was added to 3'-chloro-3-methoxystilbene (d), and heated with stirring at 180° C. for 3 hours. The reaction solution was extracted with ethyl acetate, and the resulting ethyl acetate extract was purified by silica gel chromatography (solvent: hexane/ethyl acetate=8.5/1.5 (V/V)) to obtain 3'-chloro- 3-hydroxystilbene (compound 4).

Also for compounds 3, 5, 6 and 7, starting materials (a) and (c) can be selected to obtain desired substances (e) through methoxy forms (d) in a similar manner. The yields of the respective resulting compounds are shown in Table 1.

The properties of compounds 3 to 7 are as shown in Table 2, and $^1$H NMR and $^{13}$H NMR spectra are as shown in FIGS. 2 to 11.

TABLE 1

| Stating material | | Reaction product | | | | Total yield |
|---|---|---|---|---|---|---|
| (a) | (c) | Methoxy form (d) | (yield) | Hydroxy form (e) | (yield) | |
| 2-Cl-C6H4-CH2Cl | 2-OHC-C6H4-3-OCH3 | 2'-Cl-stilbene-3-OMe | (55.8%) | 2'-Cl-stilbene-3-OH (3) | (15.0%) | 8.4% |
| 3-Cl-C6H4-CH2Cl | 2-OHC-C6H4-3-OCH3 | 3'-Cl-stilbene-3-OMe | (40.3%) | 3'-Cl-stilbene-3-OH (4) | (88.0%) | 35.5% |
| 4-Cl-C6H4-CH2Cl | 2-OHC-C6H4-3-OCH3 | 4'-Cl-stilbene-3-OMe | (29.0%) | 4'-Cl-stilbene-3-OH (5) | (70.0%) | 20.3% |
| 3,4-Cl2-C6H3-CH2Cl | 2-OHC-C6H4-3-OCH3 | 3',4'-Cl2-stilbene-3-OMe | (39.1%) | 3',4'-Cl2-stilbene-3-OH (6) | (95.4%) | 37.3% |
| 3,5-Cl2-C6H3-CH2Cl | 2-OHC-C6H4-3-OCH3 | 3',5'-Cl2-stilbene-3-OMe | (84.3%) | 3',5'-Cl2-stilbene-3-OH (7) | (93.0%) | 78.4% |

TABLE 2

| Compound No. | Compound (Structural formula) | Configuration | Melting point | Ultraviolet absorption spectrum |
|---|---|---|---|---|
| 3 | 2'-Chloro-3-hydroxystilbene | White powdery crystal | 61–62° C. | $\lambda_{max}$ = 296 nm ($\epsilon$ = 18450, EtOH) |
| 4 | 3'-Chloro-3-hydroxystilbene | White powdery crystal | 49–51° C. | $\lambda_{max}$ = 297 nm ($\epsilon$ = 24045, EtOH) |
| 5 | 4'-Chloro-3-hydroxystilbene | White powdery crystal | 130–132° C. | $\lambda_{max}$ = 299 nm ($\epsilon$ = 34341, EtOH) |
| 6 | 3',4'-Dichloro-3-hydroxy-stilbene | White powdery crystal | 120–122° C. | $\lambda_{max}$ = 300 nm ($\epsilon$ = 27412, EtOH) |

TABLE 2-continued

| Compound No. | Compound (Structural formula) | Configuration | Melting point | Ultraviolet absorption spectrum |
|---|---|---|---|---|
| 7 | 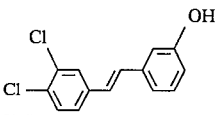 3',5'-Dichloro-3-hydroxy-stilbene | White powdery crystal | 98.5–100° C. | $\lambda_{max}$ = 300 nm ($\epsilon$ = 24970, EtOH) |

EXAMPLE 2

Nematicidal Activity of Compounds 3 to 7 against Pine Wood Nematodes

Nematicidal Activity Test 200 to 400 pine wood nematodes were placed in a dish for counting (having a diameter of 4 cm). On the other hand, distilled water was added to a solution of the nematicidal compound in ethanol until the total volume reached 4 ml, finally preparing a 2% ethanol aqueous solution of the sample. As the samples, pinosylvin monomethyl ethers (compounds 1 and 2) previously proposed, the chlorinated hydroxystilbenes (compounds 3 to 7) of the present invention and commercial nematicides against pine wood nematodes were used.

On the other hand, as a control test, a 2% ethanol aqueous solution containing no sample was used. The number of survival nematodes after 24 hours and 48 hours was counted, and the relative lethal rate to the control test was determined. The nematicidal activity was indicated by the relative lethal rate. Results thereof are shown in Table 3.

TABLE 3

| Compound No. | Structural formula | Lethal rate of pine wood nematodes (%) (after 2 days) | | | | | | | | |
|---|---|---|---|---|---|---|---|---|---|---|
| | | 100 ppm | 50 ppm | 10 ppm | 5 ppm | 2 ppm | 1 ppm | 0.5 ppm | 0.2 ppm | 0.1 ppm |
| 1 | 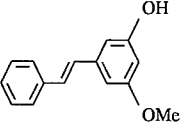 | 100 | 100 | 100 | 88 | 11 | — | — | — | — |
| 2 | 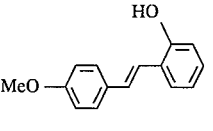 | 100 | 100 | 100 | 100 | 100 | 95 | 44 | — | — |
| 3 | 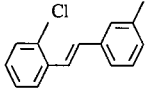 | — | — | 100 | 100 | 100 | 50 | 20 | — | — |
| 4 | 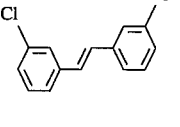 | — | — | 100 | 100 | 100 | 100 | 100 | — | 45 |
| 5 | 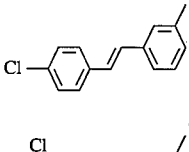 | — | — | 100 | 100 | 100 | 100 | 100 | — | 33 |
| 6 | 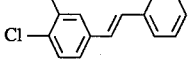 | — | — | — | — | — | — | 100 | 100 | 51 |

TABLE 3-continued

| Compound | | Lethal rate of pine wood nematodes (%) (after 2 days) | | | | | | | | |
| --- | --- | --- | --- | --- | --- | --- | --- | --- | --- | --- |
| No. | Structural formula | 100 ppm | 50 ppm | 10 ppm | 5 ppm | 2 ppm | 1 ppm | 0.5 ppm | 0.2 ppm | 0.1 ppm |
| 7 | Cl-C6H3(Cl)-CH=CH-C6H4-OH | — | — | — | 100 | 100 | 76 | 21 | — | 9 |
| goods on the market | Mesulfenfos | 67 | — | 30 | — | — | 0.5 | — | — | — |
| | Morantel tartrate | 99 | — | 46 | — | — | 1.4 | — | — | — |
| | Levamisole hydrochloride | 96 | — | 63 | — | — | 24 | — | — | — |

The results shown in Table 3 reveals that 3-hydroxy-2'-chlorostilbene (compound 3), 3-hydroxy-3'-chlorostilbene (compound 4), 3-hydroxy-4'-chlorostilbene (compound 5), 3-hydroxy- 3',4'-dichlorostilbene (compound 6) and 3-hydroxy- 3',5'-dichlorostilbene (compound 7) exhibit an effective nematicidal activity in diluted solutions and are excellent as nematicides against pine wood nematodes. They also shows that compounds 4, 5 and 6 are more excellent in their activity. Of the compounds, compound 6 showed a nematicidal activity 5 times higher than 4'-methoxy-2-hydroxystilbene (compound 2) which showed the highest activity in the prior application.

EXAMPLE 3

Each of the chlorinated hydroxystilbenes is dissolved in an organic solvent to provide a desired content, and the solution is enclosed in ampoules to prepare an injection formulation with which tracheids of pine trees are injected.

EXAMPLE 4

3',4'-Dichloro-3-hydroxystilbene is mixed with another known carrier to provide a desired content, thereby preparing a dust formulation or a liquid formulation.

The chlorinated hydroxystilbenes have an excellent activity as nematicides against pine wood nematodes. In particular, the nematicides of the present invention exhibit an effective activity even when they are used in small amounts.

What is claimed is:

1. A nematicide against pine wood nematodes containing a chlorinated hydroxystilbene or a salt thereof.

2. The nematicide as claimed in claim 1, in which said chlorinated hydroxystilbene is 2'-chloro-3-hydroxystilbene, 3'-chloro-3-hydroxystilbene, 4'-chloro-3-hydroxystilbene, 3',4'-dichloro-3-hydroxystilbene or 3',5'-dichloro-3-hydroxystilbene.

3. A method for preparing a chlorinated hydroxystilbene or a salt thereof comprising synthesizing a chlorinated methoxystilbene from a chlorinated benzyl chloride compound and a methoxybenzaldehyde by the Wittig-Horner reaction, performing demethylation to obtain the chlorinated hydroxystilbene, and preparing the salt thereof by a conventional method, if necessary.

* * * * *